US008552102B2

(12) United States Patent
Noami et al.

(10) Patent No.: US 8,552,102 B2
(45) Date of Patent: *Oct. 8, 2013

(54) COATING COMPOSITION (75) Inventors: Makoto Noami, Amagasaki (JP);
Toshiro Fujii, Amagasaki (JP);
Yoshihiro Furuya, Amagasaki (JP);
Noboru Hoshi, Osaka (JP); Toshio Shimamoto, Osaka (JP); Shunji Uramatsu, Osaka (JP)

(73) Assignees: Shionogi & Co., Ltd., Osaka (JP);
Nisshin Kasei Co., Ltd., Osaka (JP);
Daido Chemical Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,879

(22) Filed: Aug. 31, 2012

(65) Prior Publication Data
US 2012/0329936 A1  Dec. 27, 2012

Related U.S. Application Data

(62) Division of application No. 10/567,739, filed as application No. PCT/JP2004/011275 on Aug. 5, 2004, now Pat. No. 8,277,844.

(30) Foreign Application Priority Data

Aug. 20, 2003 (JP) ................................. 2003-296806

(51) Int. Cl.
*C08F 8/00* (2006.01)
(52) U.S. Cl.
USPC ........... 524/459; 524/557; 524/560; 524/599; 525/59; 424/482

(58) Field of Classification Search
USPC ............................................ 524/459; 525/59
See application file for complete search history.

(56) References Cited

U.S. PATENT DOCUMENTS

| 3,656,884 A | 4/1972 | Okaya et al. |
| 4,102,946 A | 7/1978 | Imura et al. |
| 4,320,040 A | 3/1982 | Fujita et al. |

(Continued)

FOREIGN PATENT DOCUMENTS

| EP | 0 130 717 | 1/1985 |
| EP | 1 323 404 | 7/2003 |

(Continued)

OTHER PUBLICATIONS

Hoshi et al., "Development of PVA Copolymer Capsules", Pharmaceutical Technology Europe, 2004, 16(4), 37-43, 45-46.*

(Continued)

*Primary Examiner* — Nicole M Buie-Hatcher
(74) *Attorney, Agent, or Firm* — Wenderoth, Lind & Ponack, L.L.P.

(57) ABSTRACT

The present invention relates to a novel resin composition useful as a coating agent or a binder for medicines, drugs for animals, agricultural chemicals, fertilizers, foods or the like, which contains a polyvinyl alcohol copolymer as a main component. More particularly, the present invention relates to a resin composition, characterized in that the composition is obtained by copolymerizing a polyvinyl alcohol having an average polymerization degree of 1300 or less, and at least one polymerizable vinyl monomer in a weight ratio of 6:4 to 9:1.

20 Claims, 3 Drawing Sheets

(56) References Cited

U.S. PATENT DOCUMENTS

| | | | |
|---|---|---|---|
| 4,341,563 | A | 7/1982 | Kurihara et al. |
| 4,432,965 | A | 2/1984 | Keith et al. |
| 4,912,184 | A | 3/1990 | Akasaki et al. |
| 4,912,186 | A | 3/1990 | Ohhara et al. |
| 6,001,391 | A | 12/1999 | Zeidler et al. |
| 6,967,026 | B2 | 11/2005 | Hoshi et al. |
| 8,277,844 | B2 * | 10/2012 | Noami et al. .......... 424/482 |
| 2002/0042466 | A1 | 4/2002 | Angel et al. |
| 2002/0103285 | A1 | 8/2002 | Jordan et al. |
| 2003/0059649 | A1 | 3/2003 | Saliba et al. |
| 2003/0166763 | A1 | 9/2003 | Hoshi et al. |

FOREIGN PATENT DOCUMENTS

| | | |
|---|---|---|
| JP | 60-255811 | 12/1985 |
| JP | 62-288076 | 12/1987 |
| JP | 63-108016 | 5/1988 |
| JP | 02-008271 | 1/1990 |
| JP | 09-302595 | 11/1997 |
| JP | 2002-105383 | 4/2002 |
| JP | 2003509339 W * | 3/2003 |
| WO | 02/18494 | 3/2002 |
| WO | WO 0217848 A1 * | 3/2002 |

OTHER PUBLICATIONS

International Search Report issued Sep. 7, 2004 in corresponding International Application No. PCT/JP2004/011275.
International Preliminary Report on Patentability issued Nov. 15, 2005 in corresponding International Application No. PCT/JP2004/011275.
Supplementary European Search Report issued Aug. 25, 2008 in corresponding European Application No. EP 04 74 8254.
International Search Report issued Feb. 10, 2006 in corresponding International Application No. PCT/JP2004/011275.
Machine translation of JP 2002-105383 A, Saiden Chemical Industry Co., Ltd, Oct. 2008.
Introduction of Polymer Drug, and its English translation (1992).
JP Master File of POVACOAT™ and its English translation (2005).
Manufacturing Pharmacy (1987).
Material from http://www.capsugel-jp.com/knowledge/process.html (2011).
Relation between concentration/polymerization degree and viscosity of PVA copolymer manufactured by way of trial for base material of capsule (Assumption of concentration/polymerization degree suitable for coating agent), and Relation between concentration and viscosity of two kinds of PVA copolymers manufactured by way of trial for coating (2012).
Viscosity of coating solution, and Relation between concentration and viscosity of PVA copolymer (2012).

* cited by examiner

Uncoated tablet          PVA-coated tablet

COATING COMPOSITION

This application is a divisional application of U.S. application Ser. No. 10/567,739, filed Mar. 27, 2006 now U.S. Pat. No. 8,277,844, which is the national phase filing of International Patent Application No. PCT/JP2004/011275, filed Aug. 5, 2004.

TECHNICAL FIELD

The present invention relates to a novel resin composition, more particularly, a composition useful in coating medicines, drugs for animals, agricultural chemicals, fertilizers, foods and the like, which contains a polyvinyl alcohol polymer as a main component.

BACKGROUND ART

Previously, polyvinyl alcohol (hereinafter, also abbreviated as PVA) has been extensively used as a dispersant, an adhesive, a paste glue agent, a film, a paper processing agent, a coating agent or the like in various fields. For example, Encyclopedia of Pharmaceutical Excipients lists use of a partially hydrolyzed polyvinyl alcohol as a coating agent since it has water solubility and film forming property. However, when this is used by a spray method which is a conventional coating means, coating is very difficult due to remarkably spinnability (a finely-divided mist is not obtained but a spider web is obtained), and the partially hydrolyzed polyvinyl alcohol has scarcely been put into practice.

The present inventors have found that a polyvinyl alcohol polymer obtained by copolymerizing (hereinafter, also referred to as PVA copolymer), for example, emulsion-polymerizing polyvinyl alcohol, particularly, partially hydrolyzed polyvinyl alcohol with a polymerizable vinyl monomer, for example, acrylic acid and methyl methacrylate is easily dissolved in water, and it becomes possible to coat the solution with a conventional pneumatic spray nozzle without exhibiting spinnability. The present inventors have found that since a film of the thus obtained PVA copolymer is colorless, transparent, has no taste and no smell, and is excellent in physical properties such as strength, elongation rate and adhesive property, and has the property that gas permeability to oxygen is extremely low, the film is useful in protection of an easily oxidizable drug, masking of medicines, agricultural chemicals and foods having an offensive smell, suppression of whisker formation of a drug having sublimation property, use as an excellent binder for an oral solid preparation, or masking of drugs or foods exhibiting bitterness.

In addition, since such PVA copolymer has another characteristic that it is excellent in solubility in a solvent, and its solution has a remarkably low adhesive property, it is possible to coat fine particles such as fine granules and bulk therewith. By utilizing such excellent nature of the PVA copolymer, it has become possible to develop high concentration coating which can prevent interaction with other agent, modify a surface of a bulk, mask an offensive smell or bitterness and remarkably shorten a coating time has become possible.

Further, WO 02/17848 discloses an invention of a hard capsule with excellent stability, containing a PVA copolymer as a main component, said hard capsule being prepared by filling a solution of a hardly soluble pharmaceutical component or a semi-solid into a capsule, but there has been no example of use of the PVA copolymer in coating medicines, drugs for animals, agricultural chemicals, fertilizers, foods and the like.

As described above, application range of the PVA copolymer as a coating agent is far wider as compared with other known coating agents which are currently used as a general-purpose polymer for film coating, and such PVA copolymer has excellent property. Accordingly, it can be expected that the PVA copolymer will serve as a substitute for such known coating agents in the future. In addition, as a result of various safety tests, any problem regarding safety has not been recognized until now in this PVA copolymer.

DISCLOSURE OF THE INVENTION

Since a partially hydrolyzed polyvinyl alcohol has water solubility and film formability, use of the compound as a coating agent is listed in Handbook of Pharmaceutical Excipients. However, when this is used by a spray method which is a conventional coating means, coating is very difficult due to remarkable spinnability (a finely-divided mist is not obtained, but a spider web is obtained), and thus the compound has scarcely been put into practice. In view of such circumstances, development of a composition for coating medicines, agricultural chemicals, foods and the like, which has not the aforementioned defects and has excellent properties, has been demanded.

In view of the aforementioned problems, the present inventors have intensively studied and, as a result, found that an aqueous solution of a polyvinyl alcohol copolymer obtained by copolymerizing polyvinyl alcohol or a derivative thereof with a polymerizable vinyl monomer can be coated with a conventional pneumatic spray nozzle without exhibiting spinnability. The present inventors have found that since a film of the thus obtained PVA copolymer is colorless, transparent, and excellent in physical properties such as strength, elongation rate and adhesiveness, and has a very low penetration of gas such as oxygen, and the like, such film is useful in protection of easily oxidizable drugs, masking of medicines, drugs for animals agricultural chemicals, fertilizers, and foods having an offensive smell, suppression of whisker formation of drugs having sublimation property, and use as an excellent binder for oral solid preparations. The present invention has been completed based on these findings.

That is, the present invention relates to:

(1) a resin composition characterized in that it is obtained by copolymerizing a polyvinyl alcohol having an average polymerization degree of 1300 or less, and at least one or more polymerizable vinyl monomer (s) in a weight ratio of 6:4 to 9:1, (2) the resin composition according to (1), wherein the polyvinyl alcohol has an average polymerization degree of 900 or less, (3) the resin composition according to (1), wherein the polyvinyl alcohol has an average polymerization degree of 200 to 600, (4) the resin composition according to any one of (1) to (3), wherein the polyvinyl alcohol is a partially hydrolyzed polyvinyl alcohol, (5) the resin composition according to any one of (1) to (4), wherein the polymerizable vinyl monomer is selected from an unsaturated carboxylic acid, an unsaturated carboxylic acid ester, an unsaturated nitrile, an unsaturated amide, an aromatic vinyl, an aliphatic vinyl, an unsaturated bond-containing heterocycle and a salt thereof, (6) the resin composition according to any one of (1) to (4), wherein the composition is obtained by copolymerizing 2 or more polymerizable vinyl monomers, and at least one of said vinyl monomers is an unsaturated carboxylic acid or a salt thereof and at least one of said vinyl monomers is an unsaturated carboxylic acid ester, (7) the resin composition according to (6), wherein the unsaturated carboxylic acid or a salt thereof is selected from the group consisting of acrylic acid, methacrylic acid, crotonic acid, fumaric acid, maleic acid, itaconic acid and a salt thereof, and the unsaturated carboxylic acid ester is selected from the group consisting of methyl methacrylate, methyl acrylate, ethyl methacrylate, ethyl acrylate, butyl methacrylate, butyl acrylate, isobutyl methacrylate, isobutyl acrylate, cyclohexyl methacrylate, cyclohexyl acrylate, 2-ethylhexyl methacrylate, 2-ethylhexyl acrylate, hydroxyethyl methacrylate, hydroxyethyl acrylate, an ester of polyethylene glycol and methacrylic acid, an ester of polyethylene glycol and acrylic acid, and an ester of polypropylene glycol and acrylic acid, (8) the resin composition according to (7), wherein the unsaturated carboxylic acid, its salt and the unsaturated carboxylic acid ester are those represented by the general formula (I):

$$H_2C=C(R_1)-COOR_2 \qquad (I)$$

(wherein $R_1$ represents a hydrogen atom or a methyl group, and $R_2$ represents a hydrogen atom or an alkyl group having 1 to 4 carbon atoms), or a salt thereof, (9) the resin composition according to (8), wherein the unsaturated carboxylic acid or a salt thereof is acrylic acid or a salt thereof, and the unsaturated carboxylic acid ester is methyl methacrylate, (10) the resin composition according to (9), wherein the weight ratio of acrylic acid or a salt thereof and methyl methacrylate in the copolymerization is 3:7 to 0.5:9.5, (11) the resin composition according to any one of (1) to (4), characterized in that the composition is obtained by copolymerizing a partially hydrolyzed polyvinyl alcohol having an average polymerization degree of 300 to 500 and a polymerizable vinyl monomer in a weight ratio of 6:4 to 9:1, wherein said polymerizable vinyl monomer is a combination of acrylic acid and methyl methacrylate combined in the weight ratio of 3:7 to 0.5:9.5 in the copolymerization, (12) the resin composition according to any one of (1) to (4), wherein the weight ratio of the partially hydrolyzed polyvinyl alcohol having an average polymerization degree of 300 to 500, methyl methacrylate and acrylic acid in the copolymerization is 60 to 90:7 to 38:0.5 to 12, (13) a coating agent, comprising the resin component according to any one of (1) to (12), (14) a coating agent for medicines, animal drugs, agricultural chemicals, fertilizers or foods, comprising the resin composition according to any one of (1) to (12), (15) a medicine, an animal drug, an agricultural chemical, a fertilizer or a food, which is coated with the coating agent according to (14), (16) a binder, comprising the resin composition according to any one of (1) to (12), (17) a resin composition, characterized in that said composition is obtained by copolymerizing a polyvinyl alcohol having an average polymerization degree of 900 or less, and at least one or more polymerizable vinyl monomer(s) selected from the group consisting of (a) an unsaturated carboxylic acid selected from acrylic acid, crotonic acid, fumaric acid, maleic acid and itaconic acid, or a salt thereof and (b) an unsaturated carboxylic acid ester selected from methyl methacrylate, methyl acrylate, ethyl methacrylate, ethyl acrylate, butyl methacrylate, butyl acrylate, isobutyl methacrylate, isobutyl acrylate, cyclohexyl methacrylate, cyclohexyl acrylate, 2-ethylhexyl methacrylate, 2-ethylhexyl acrylate, an ester of polyethylene glycol and methacrylic acid, an ester of polyethylene glycol and methacrylic acid, and an ester of polypropylene glycol and acrylic acid in a weight ratio of 6:4 to 9:1, provided that a copolymer of a polyvinyl alcohol and a polymerizable vinyl monomer capable of forming a chemical bond when reacted with a carboxyl group is excluded, and a copolymer of a polyvinyl alcohol having an average polymerization degree of 1500 or 1700 and an unsaturated carboxylic acid, a salt thereof, and an unsaturated carboxylic acid ester is excluded, (18) the resin composition according to (17), wherein the unsaturated carboxylic acid or a salt thereof is acrylic acid or a salt thereof, and the unsaturated carboxylic acid ester is methyl methacrylate, and (19) a coating agent for tablets or granules, comprising the resin composition according to (17) or (18).

EFFECTS OF THE INVENTION

The coating composition of the present invention containing a polyvinyl alcohol copolymer as a main component has effects of preventing oxidation of medicines, drugs for animals, agricultural chemicals, fertilizers and foods, masking an offensive smell, preventing a change in the formulation, and of preventing bitterness. The coating composition is extremely useful, because of its various excellent effects such as improvement in adhesiveness to preparations, coating effect by fine particles, and easy implementation of coating at a high concentration. That is, in the case where a component constituting a medicament, an animal drug, an agricultural chemical, a fertilizer or a food contains an easily oxidizable component, a component having an offensive smell, two or more kinds of components which deteriorate preservation stability when combined, or a component having an offensive taste such as bitterness, such drawbacks of these components can be easily eliminated by coating the whole of these components or preparations with the resin composition of the present invention.

In addition, it is known that whisker formation occurs in a preparation containing a drug having sublimation property (e.g. caffeine, aspirin) during its preservation. There are an example wherein a whisker is formed from a preparation itself, causing a change in appearance, and an example wherein clouding occurs directly in the inner surface of a PTP package which is a package container, or a glass bottle, resulting in remarkable deterioration of product value. This cannot be suppressed by a conventional film coating method, and is a phenomenon over which pharmacy researcher is suffering from strategy. However, the PVA copolymer of the present invention has excellent effect of suppressing a whisker formation by film-coating on a pharmaceutical preparation having sublimation property. Herein, a whisker is a phenomenon in which a crystal is precipitated on a preparation surface or in the vicinity of a preservation container due to sublimation.

Further, in the production of medicines, particularly, an oral solid preparation (e.g. granule, tablet), it is known to use various binders. However, these known binders have many problems, and have not necessarily satisfactory function. That is, a certain kind of binders react with a drug and are colored and, when one tries to obtain a sufficient granule strength or tablet hardness, a large amount of formulation becomes necessary. As a result, the dissolution rate of a drug is delayed and, further, since its binding force is deteriorated, or conversely increased with time, a crack or a breakage of a granule or a tablet is generated, and fatal defects as a preparation such as delay of disintegration and dissolution rate are generated in some cases. However, by using the PVA copolymer of the present invention as a binder, a sufficient binding force is exerted even at a small amount and, moreover, even when preserved for a long period of time, both of appearance and strength of a granule or a tablet are not changed, and sufficient dissolution property can be obtained.

Further, the resin composition of the present invention is excellent in adhesiveness to a component or a preparation as compared with the previous composition, and even when a component or a preparation is a fine particle, the composition can be easily coated at a high concentration upon coating, and the composition has characteristic that adhesive property to a preparation is excellent.

Such the effect is a new unexpected finding obtained by results of many trial and error studies by the present inventors.

BEST MODE FOR CARRYING OUT THE INVENTION

A polyvinyl alcohol copolymer which is used as a main component in the coating composition of the present invention can be prepared by copolymerizing polyvinyl alcohol or a derivative thereof and at least one kind of polymerizable vinyl monomer by the per se known method.

Examples of a method of preparing such the polyvinyl alcohol copolymer include the per se known method such as radical polymerization, for example, solution polymerization, suspension polymerization, emulsion polymerization and bulk polymerization, and said method can be performed under each conventional polymerization condition. This polymerization reaction is usually performed in the presence of a polymerization initiator and, if necessary, in the presence of a reducing agent (e.g. sodium erysorbate, sodium metabisulfite, ascorbic acid), a chain transfer agent (e.g. 2-mercaptoethanol, α-methylstyrene dimer, 2-ethylhexyl thioglycolate, laurylmercaptan) or a dispersant (e.g. surfactant such as sorbitan ester, lauryl alcohol) in water, an organic solvent (e.g. methanol, ethanol, cellosolve, carbitol) or a mixture thereof. In addition, a method of removing an unreacted monomer, a drying method, a grinding method and the like may be, but not limited to, the known methods.

Polyvinyl alcohol which is a raw material of the polyvinyl alcohol copolymer of the present invention is a partially hydrolyzed polyvinyl alcohol having an average polymerization degree of about 200 to 1500, preferably about 200 to 1300, more preferably about 200 to 900, further more preferably about 200 to 600, and most preferably about 300 to 500, and a hydrolyzation degree of about 60 to 100 mole %, preferably 78 to 96 mole %. Such the hydrolyzed polyvinyl alcohol can be prepared by radical-polymerizing vinyl acetate, and appropriately hydrolyzing the resulting vinyl acetate. In order to prepare a desired polyvinyl alcohol, this is attained by appropriately controlling a polymerization degree and a hydrolyzation degree by the per se known method.

A commercially available product of such partially hydrolyzed polyvinyl alcohol can be used, and examples of a commercially available product of preferable polyvinyl alcohol include Gosenol EG05, EG25 (manufactured by The Nippon Gohsei Co., Ltd.), PVA203 (manufactured by Kuraray Co., Ltd.), PVA204 (manufactured by Kuraray Co., Ltd.), PVA205 (manufactured by Kuraray Co., Ltd.), JP-04 (manufactured by JAPAN VAM & POVAL CO., LTD), and JP-05 (manufactured by JAPAN VAM & POVAL CO., LTD). In the production of the polyvinyl alcohol copolymer which is a main component of the present composition, polyvinyl alcohol as a raw material may be used alone or in an appropriate combination of two or more kinds of polyvinyl alcohols having different polymerization degrees and hydrolyzation degrees, depending on the purpose. For example, polyvinyl alcohol having an average polymerization degree of 300 and polyvinyl alcohol having an average polymerization degree of 1500 can be mixed and used.

In the present invention, various modified polyvinyl alcohols can be used as a raw material, a polyvinyl alcohol, and examples include an amine-modified polyvinyl alcohol, an ethylene-modified polyvinyl alcohol, a carboxylic acid-modified polyvinyl alcohol, a diacetone-modified polyvinyl alcohol, and a thiol-modified polyvinyl alcohol. These modified polyvinyl alcohols can be a commercially available product, or a product prepared by the method known in the art.

Examples of the polymerizable vinyl monomer to be polymerized with a polyvinyl alcohol as a raw material include unsaturated carboxylic acids such as acrylic acid, methacrylic acid, crotonic acid, fumaric acid, maleic acid, itaconic acid and the like or a salt thereof (e.g. alkali metal salt, ammonium salt, alkylamine salt), esters thereof (e.g. substituted or unsubstituted alkyl ester, cyclic alkyl ester, polyalkylene glycol ester), unsaturated nitriles, unsaturated amides, aromatic vinyls, aliphatic vinyls, unsaturated bond-containing heterocycles and the like. Specific examples include (1) as acrylic acid esters, for example, methyl acrylate, ethyl acrylate, butyl acrylate, isobutyl acrylate, cyclohexyl acrylate, 2-ethylhexyl acrylate, hydroxyethyl acrylate, polyethylene glycol acrylate (ester of polyethylene glycol and acrylic acid), polypropylene glycol acrylate (ester of polypropylene glycol and acrylic acid), (2) as methacrylic acid esters, for example, methyl methacrylate, ethyl methacrylate, butyl methacrylate, isobutyl methacrylate, cyclohexyl methacrylate, 2-ethylhexyl methacrylate, hydroxyethyl methacrylate, polyethylene glycol methacrylate (ester of polyethylene glycol and methacrylic acid), (3) as unsaturated nitriles, for example, acrylonitrile, and metaacrylonitrile, (4) as unsaturated amides, for example, acrylamide, dimethylacrylamide, and methacrylamide, (5) as aromatic vinyls, styrene, and α-methylstyrene, (6) as aliphatic vinyls, vinyl acetate, (7) as unsaturated bond-containing heterocycles, N-vinylpyrrolidone, and acryloylmorpholine.

These polymerizable vinyl monomers, alone or in combination of two or more kinds, can be copolymerized with a polyvinyl alcohol and, as a preferable combination, a mixture of acrylic acid and methacrylic acid ester (e.g. methyl methacrylate) may be copolymerized with a polyvinyl alcohol. Herein, in the copolymerization of a polyvinyl alcohol and a copolymerizable vinyl monomer, the weight ratio of each component is about 6:4 to 9:1, preferably about 8:2. In addition, when acrylic acid and methyl acrylate are used as a polymerizable vinyl monomer, the weight ratio thereof is about 3:7 to about 0.5:9.5, preferably about 1.25:8.75. A preferable polyvinyl alcohol copolymer used as a main component of the coating composition in the present invention consists of polyvinyl alcohol (average polymerization degree about 200 to 1300), methyl methacrylate and acrylic acid, and the weight ratio thereof is about 60-90:7-38:0.5-12, preferably about 80:17.5:2.5.

In addition, the weight ratio of polyvinyl alcohol, methyl methacrylate and acrylic acid upon copolymerization is the same as the weight ratio of polyvinyl alcohol, methyl methacrylate and acrylic acid in the copolymer, and is 60-90:7-38:0.5-12. This polymerization ratio can be measured by NMR.

As a polymerization initiator, polymerization initiators which are used in the art can be used. Examples of such initiator include inorganic peroxides such as potassium persulfate, ammonium persulfate, hydrogen peroxide and the like, organic peroxides such as peracetic acid, tertiary butyl hydroperoxide, di-n-propyl peroxydicarbonate and the like, and azo compounds such as 2,2'-azobis(2-amidinopropane) hydrochloride, 2,2'-azobis(2,4-dimethylvaleronitrile) and the like.

The coating composition of the present invention can take a variety of forms and, generally, upon actual application to medicines, drugs for animals, agricultural chemicals, fertilizers, foods and the like, the composition is preferably applied by means of scattering, spraying or the like in the form of an aqueous solution, an aqueous suspension, an organic solvent solution or an organic solvent dispersion.

The coating composition of the present invention has effect of masking an offensive smell of medicines, drugs for animals, agricultural chemicals, fertilizers, foods or the like, examples of such the offensive smell include peculiar offensive smell or stimulating smell derived from medicines (e.g. L-cysteine, thiamine hydrochloride, methionine, digestion enzyme preparations, various crude drugs) or agricultural chemicals, and an offensive smell derived from various foods (e.g. fish smell, retort smell, animal meat smell etc.), and the composition is effective in suppressing such the smell. In addition, the composition also has effect of masking bitterness of medicines, foods and the like, and examples of medicines exhibiting such the bitterness include acetaminophen, pyridoxine hydrochloride, anhydrous caffeine, chlorpromazine, erythromycin, phenobarbitar, and promethazine hydrochloride. Further, by applying the coating composition of the present invention to unstable medicines for which interaction with other preparation is feared, for example, isopropylantipyrine and acetaminophen which cause melting point depression by mixing, or phenylpropanolamine and chlorphenylamine maleate which are discolored by mixing, such the interaction can be prevented.

Further, since the coating composition of the present invention also has the oxygen penetration preventing effect, the composition is useful in coating medicines which easily undergo oxidative degradation (e.g. ascorbic acid, vitamin A, vitamin E, etc.), animal drugs, agricultural chemicals, fertilizers, or foods.

EXAMPLES

The present invention will be explained in more detail below by describing Production Example, Working Examples and Comparative Examples, but the present invention is not limited by these Examples.

Production Example 175.8 g of PVA (EG05, polymerization degree 500, saponification degree 88%, manufactured by The Nippon Gohsei Co., Ltd.) and 582.3 g of ion-exchanged water were fed into separable flask equipped with a condensing tube, a dropping funnel, a thermometer, a nitrogen introducing tube and a stirring device, and the mixture was dispersed at a normal temperature, and then completely dissolved at 95° C. Then, 5.4 g of acrylic acid and 37.3 g of methyl methacrylate were added thereto, and the atmosphere was replaced with nitrogen gas. After the temperature was raised to 50° C., 8.5 g of tertiary butyl hydroperoxide and 8.5 g of sodium erysorbate were added thereto. The reaction was completed in 4 hours to obtain a PVA copolymer. This product was dried and ground by a conventional method to obtain a PVA copolymer powder.

Example 1

High Concentration Coating Example

Figure 1:
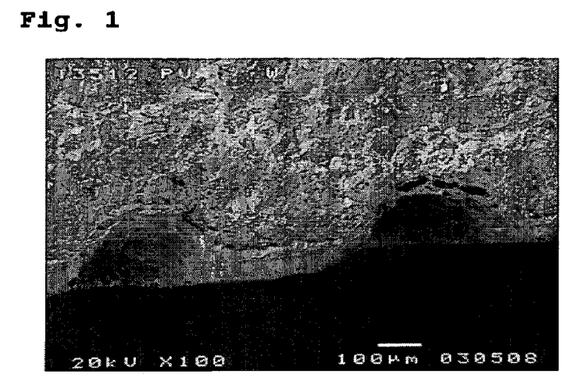
FIG. 1 shows a cross-sectional SEM photograph of an embossed part of an embossed tablet coated with the resin composition of the present invention.
Figure 2:
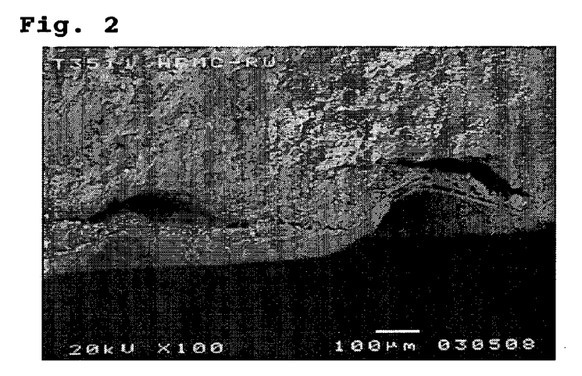
FIG. 2 shows a cross-sectional SEM photograph of an embossed part of an embossed tablet coated with the existing coating agent.

The PVA copolymer obtained in Production Example was formulated into a 14 weight % aqueous solution, and the aqueous solution of the PVA copolymer was coated on 20,000 uncoated tablets having φ7 mm and a weight of 130 mg at 4 mg/tablet using side vented type coating apparatus (HI-COATER, manufactured by Freund Corporation) having a pneumatic spray nozzle. As a result, a film-coated tablet exhibiting better appearance and disintegration property of 2 minutes and 50 seconds using water as a test solution was obtained 83 minutes after the coating. At that time, a viscosity of such coating solution showed 104 mPa·s at 25° C., and a uniform fine mist suitable in coating with a conventionally used pneumatic spray nozzle was obtained. Further, when this formulation example is applied to a tablet embossed for discrimination, as shown in a cross-sectional SEM photograph (see FIG. 1 and FIG. 2), shrinkage of a film which is seen at lack of an adhesion force to an uncoated tablet surface, and unclearness of an embossed mark accompanied with floating (bridging phenomenon) (FIG. 2), though they can be seen at the time of coating with an aqueous solution of a water-soluble cellulose derivative, were not seen, thereby to obtain a clearly embossed tablet (FIG. 1) due to the effect of better adhesive property of the present invention. An adhesion force of a coating agent to an uncoated tablet surface of both was measured with Shimadzu autograph (AG-500B) and, as a result, an adhesion force of a water-soluble cellulose derivative exhibited 0.32 N, while an adhesion force of the coating agent of the present invention exhibited 1.10 N which is about 3.4-fold, and strong adhesive property to an uncoated tablet was clearly recognized in the film of the present invention.

Disintegration property of the resulting coated tablet showed the same disintegration property regardless of the pH of a test solution such as the 1st fluid, the 2nd fluid and water in Japanese Pharmacopoeia, and the resulting coated tablet does not undergo influence due to the presence of a surfactant such as polysorbate which is added as a solubilizer in a dissolution test of a hardly soluble drug preparation. The coated preparation has a sufficient physical strength against a stress in a packaging step or market distribution. In addition, a coloring agent and a luster agent which are generally used in the formulation, and an additive for the purpose of light shielding may be blended into this formulation example, and printing on a tablet surface for discrimination is also possible.

Comparative Example 1

An aqueous solution prepared by adjusting the concentration of a solution of HPMC (hydroxypropylmethyl cellulose), which is now most widely used as a water-soluble film coating agent, to 8 weight % was coated in 4 mg/tablet on 20,000 uncoated tablets having φ7 mm and a weight of 130 mg using a side vented type coating apparatus (HICOATER, manufactured by Freund Corporation) having a pneumatic spray nozzle. As a result, a viscosity of the coating solution thereupon exhibited the approximately same viscosity of 108 mPa·s at 25° C. regardless of a low concentration of 8 weight %, relative to 14 weight % concentration of the solution in Example 1. Appearance of the coated tablet was better, and a disintegration time using water as a test solution was 3 minutes. These both results were equivalent to those of Example 1. However, the coating time required in this Comparative Example was 171 minutes, which were about 2-fold the coating time in Example 1 for coating the tablet in the same coating amount of 4 mg/tablet, due to low concentration and adhesive property of the coating solution.

Example 2

Fine Particle Coating Example 800 g of acetaminophen crystals (manufactured by Iwaki Seiyaku Co., Ltd.) having a particle diameter of 40 to 300 μm (average 135 μm) was fed into a fluidized bed coating apparatus (FD-MP-01, Powrex) having an inner cylinder. An aqueous solution (10 weight %) of a PVA copolymer having a polymerization degree of 300 prepared as in the Production Example was sprayed in a bottom spray manner under the coating condition that the solution was sprayed to particles moving in a cylinder at a high speed from a lower part of a cylinder, so that the coating was performed in 10 weight % relative to acetaminophen. The spray solution was used at room temperature, and shaking during coating was performed at arbitrary time. In addition, in order to investigate uniformity of coating, the aqueous solution was colored with Yellow No. 5 pigment (FD & C yellow #6).

Coating conditions using a fluidized bed granulator are as follows:

supply air temperature: 80° C.; drying air flow: 0.7 m³/minute; spray feed rate: 8 g/minute; exhaust air temperature: 36 to 37° C.; atomize air: 50 NL/minute; inner cylinder height: 15 mm; post-drying: 15 minutes; spray time: 96 minutes.

Figure 3:
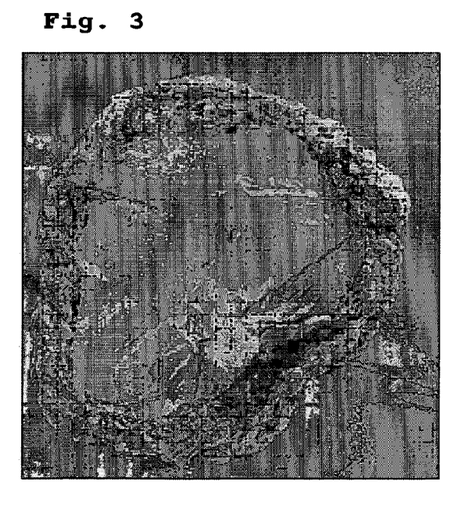
FIG. 3 shows a cross-sectional SEM photograph (×200) of acetaminophen particles coated with the resin composition of the present invention.
Figure 4:
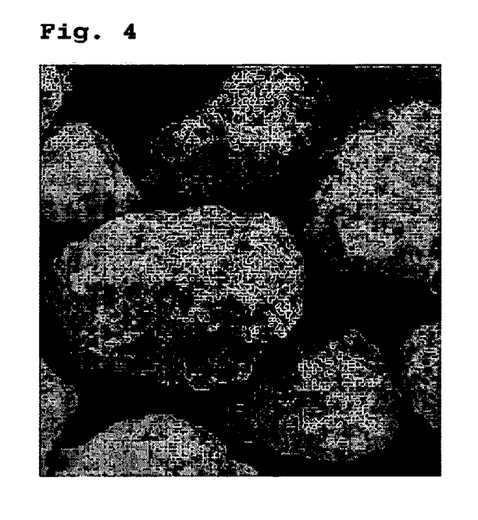
FIG. 4 shows a surface SEM photograph (×160) of acetaminophen particles coated with the resin composition of the present invention.

The aqueous PVA copolymer solution having a concentration of 10 weight % was sprayed under the above condition and, as a result, poor fluidity and crystal aggregation during spraying were not observed, resulting in always showing better fluidity, thereby to obtain a uniformly colored and coated acetaminophen. In this coated acetaminophen, bitterness occurred in its administration was alleviated as compared with an uncoated product, and the masking effect of bitterness was clearly obtained. SEM photographs of a cross-section and a surface of acetaminophen crystals coated with 10 weight % of the PVA copolymer are shown in FIG. 3 and FIG. 4, respectively, wherein aggregated particles are not seen, and a surface of crystal particles is uniformly coated with the PVA copolymer. A mixture of the same amounts of this PVA copolymer-coated acetaminophen and uncoated isopropylantipyrine, and both uncoated drugs as a control were preserved for one week under sealed condition at 60° C. and, as a result, an uncoated product caused melting point depression, and melting tendency was seen, while in a mixed product of the PVA copolymer-coated acetaminophen, abnormality was not recognized, and the coating effect on the original drug was clearly seen. This demonstrates that such coating with the PVA copolymer can prevent a content reduction caused by contact between drugs, and a change of formulation such as coloring change, which are well known to pharmacy researchers. Usually, in fine particle coating, aggregation is prevented by blending an adhesion preventing agent such as talc and fats and oils, but in coating of fine particles with the PVA copolymer, the blending is unnecessary.

Example 3

Smell Masking Example

Figure 5:
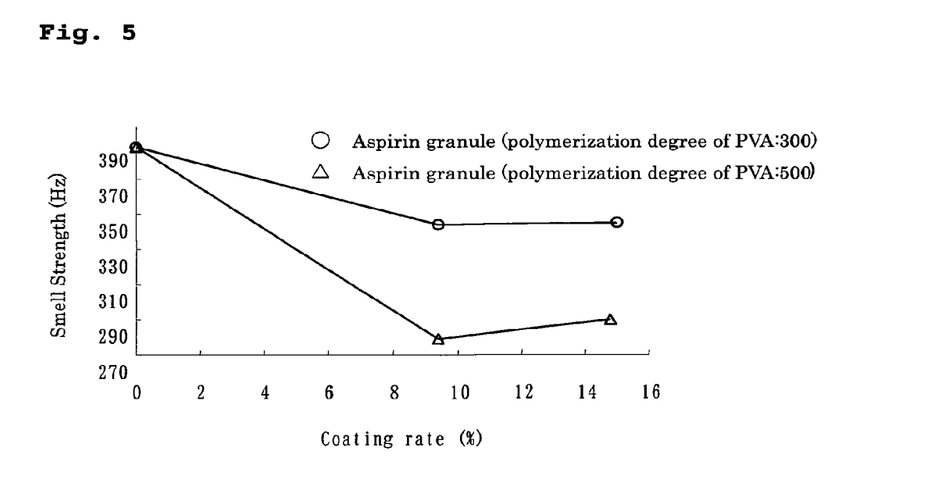
FIG. 5 shows relationship of a coating rate and a smell strength relative to an aspirin granule in accordance with the resin composition of the present invention.

A pillar granule containing 50 weight % of aspirin was prepared, and enteric coating was applied to the granule. This enteric-coated granule generates an acetic acid smell with time, and 10 weight % aqueous solutions of PVA copolymers (polymerization degree 300 and 500) prepared as in Production Example by changing starting raw materials, respectively, were spray-coated on an enteric coated granule in an amount of 10 weight %, and masking of an acetic acid smell was tried. A test was performed with a smell sensor SF-105 (manufactured by Sogo Pharmaceutical Co., Ltd.) for measuring a smell strength upon adsorption of a smell molecule onto a synthetic two-molecular film, a sensor element 112 AJ and, as a result, as shown in FIG. 5, an acetic acid smell was remarkably reduced and, particularly, when coated with a PVA copolymer having a polymerization degree of 500, masking could be done organoleptically until an acetic acid smell was not felt.

In addition, regarding a digestion enzyme preparation containing pancreatin having a peculiar smell, aqueous solutions of PVA copolymers having a polymerization degree of 300 and 500 prepared similarly to the Formulation Example were sprayed to try to mask a smell. As in the aspirin granule, a smell peculiar to the enzyme was clearly decreased when coated with the PVA copolymer having a polymerization degree of 500.

Example 4

Example of Oxygen Penetration Preventing Effect

A tablet (diameter: 10.5 mm, thickness: 4.2 mm) incorporating ascorbic acid and copper sulfate for promoting its oxidative degradation was prepared, and a 10 weight % aqueous solution (viscosity: 26 mPa·s) of a PVA copolymer having a polymerization degree of 500 prepared similarly to Example 3 was used to coat the tablet with a side vented type coating machine HICOATER (manufactured by Freund Corporation) having a pneumatic spray nozzle, for the purpose of preventing oxygen penetration. At 40° C. and a relative humidity of 70%, time course of the remaining rate of ascorbic acid was measured under atmospheric environmental condition (A) and nitrogen-replaced and oxygen-free environmental condition (B). As a comparative example, an uncoated tablet (diameter: 10.5 mm, thickness: 4.2 mm) and a coated tablet obtained by similarly coating the uncoated tablet with HPMC (hydroxypropylmethyl cellulose) which is a water-soluble film coating agent for general purpose were preserved under the environment (A) and the environment (B), respectively, and stability of ascorbic acid was compared and studied. In addition, the uncoated tablet preserved under the nitrogen-replaced and oxygen-free environment was similarly tested. A tablet composition and the coating condition are shown below.

TABLE 1

Tablet composition:

| Ascorbic acid | 100 mg |
|---|---|
| Copper sulfate | 0.1 mg |
| Lactose | 202.6 mg |
| Corn starch | 86.8 mg |
| HPC | 8.0 mg |
| Magnesium stearate | 2.5 mg |
| Total | 400.0 mg |

Coating Condition:

Coating machine: HICOATER HCT-48; spray gun: pneumatic spray; nozzles aperture diameter 0.6 mm; tablet supply: 10,000 tablets; pan rotation number: 24 rpm; spray air: 70 L/minute; spray air temperature: 60° C.; drying airflow: 3 m³/minute; exhaust air amount: 4.5 m³/minute.

Figure 6:
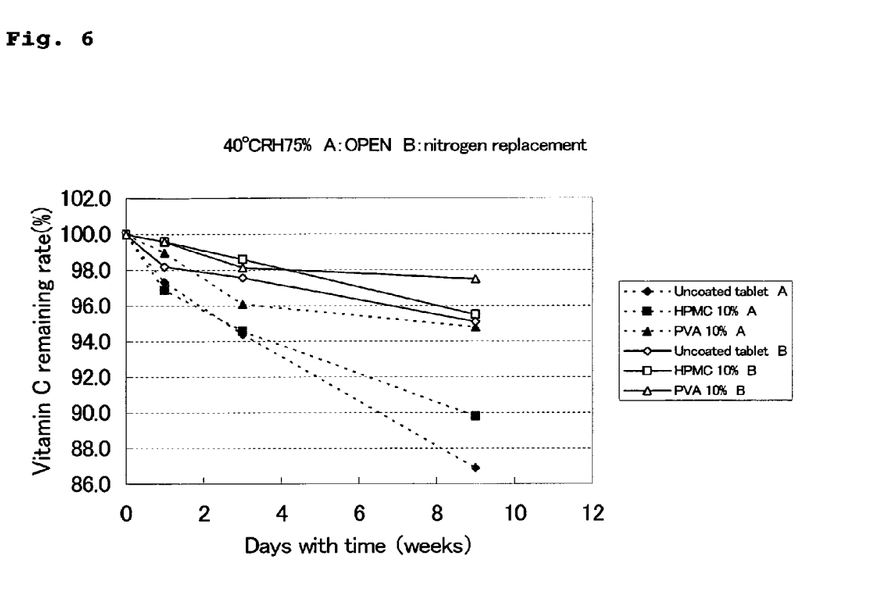
FIG. 6 shows the effect of preventing oxidative degradation of ascorbic acid in accordance with the resin composition of the present invention.

As shown in FIG. 6, the preparation coated with a water-soluble film coating agent of HPMC used for general purpose, exhibited the same extent of ascorbic acid remaining rate as that of an uncoated tablet, and the oxygen penetration preventing effect is not recognized, while in the ascorbic acid stabilizing effect, the preparation coated with the PVA copolymer showed the same extent of stability as that of an uncoated tablet preserved under oxygen-free heating and humidifying condition, and the preventing effect of high oxygen penetration was recognized.

Example 5

Sugar Coating

Twenty thousands pseudo-uncoated tablets having φ8 mm and a weight of 167 mg/tablet, which contains lactose and corn starch as a component, were supplied into a side vented type coating apparatus (HICOATER 48 type, Freund Corporation), and coating solutions 1 and 2 of the following compositions which contain a PVA copolymer (polymerization degree 500) prepared similarly to Example 2 were prepared.

In the formulation, the PVA copolymer was well compatible with an aqueous sucrose solution, and a clear syrup solution having a suitable viscosity was obtained. According to a conventional method of an automatic sugar coating, spraying of this solution with a pneumatic spray nozzle, drying without wind was repeated to coat the tablet with the coating solution 1 to an amount of 1 to 90 mg/tablet, and with the coating solution 2 to 13 mg/tablet. Further, polishing and coating procedures were applied to these tablets according to a conventional method. A composition of the coating solutions is shown below.

TABLE 2

Composition of coating solution 1:

| Sucrose | 340 g |
|---|---|
| Purified water | 322 g |
| PVA copolymer | 40 g |
| Calcium carbonate | 120 g |
| Talc | 120 g |
| Yellow No. 5 pigment (FD & C yellow #6) | 1 g |

TABLE 3

Composition of coating solution 2:

| Sucrose | 652 g |
|---|---|
| Purified water | 345 g |
| PVA copolymer | 2 g |
| Yellow No. 5 pigment | 1 g |

The resulting sugar-coated tablet had the equivalent appearance to that of a conventional preparation having a luster, and a disintegration time of a test with water was 7 to 8 minutes, demonstrating it to be a rapid disintegration.

Example 6

Whisker Suppressing Effect

A tablet (255 mg) containing 50 mg of caffeine and 30 mg of potassium guaiacolsulfonate was coated with 13 mg of the following film composition containing a PVA copolymer having an average polymerization degree of 500, which was prepared similarly to Example 3. A film composition and its coating condition are shown below.

TABLE 4

Film composition:

| PVA copolymer (average polymerization degree 500) | 10 mg |
|---|---|
| Titanium oxide | 2 mg |
| Talc | 1 mg |
| Total | 13 mg |

Figure 7:
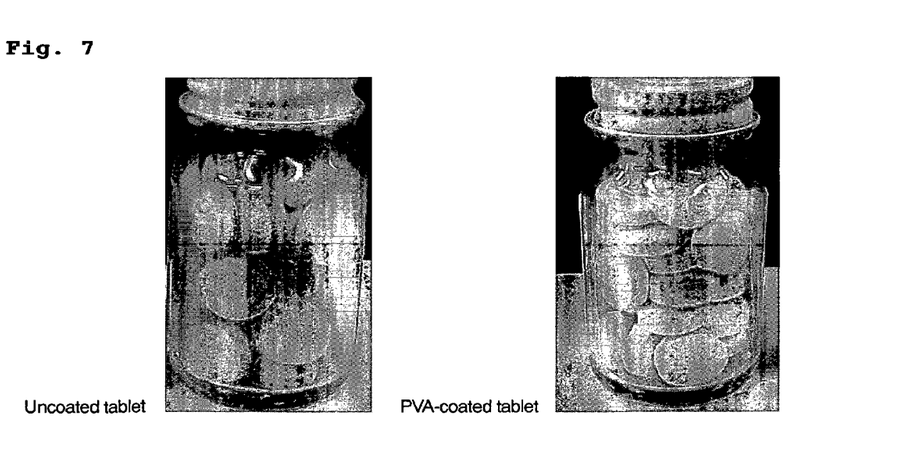
FIG. 7 shows a photograph of a clouding degree of a glass bottle due to whisker formation after preservation for one month in which a coated tablet obtained by coating a caffeine- and potassium guaiacolsulfonate-containing tablet with the resin composition of the present invention, and an uncoated tablet are warmed to 60° C. in a sealed glass bottle.

Coating Condition:

Coating machine: HICOATER HCT-48; spray gun: pneumatic spray; nozzle aperture diameter 0.6 mm; tablet supply: 17000 tablets; pan rotation number: 20 rpm; spray air: 70 L/minute; drying airflow: 55° C.; airflow amount: 2.5 m³/minute; exhaust air amount: 4.5 m³/minute As shown in FIG. 7, the resulting PVA copolymer-coated tablets and uncoated tablets were warmed to 60° C. in a sealed glass bottle and, as a result, in the glass bottle in which the uncoated tablets were preserved, clouding due to a whisker was generated in one month, while no change was recognized in the PVA copolymer-coated tablets.

Example 7

Example Using Binder for Granules and Tablets

1. Granules

The PVA copolymer having a polymerization degree of 300 obtained in Production Example was dissolved in water to make a 5 weight % aqueous solution, and 1.4 kg of the 5 weight % aqueous solution was added to a total 7 kg of a mixed powder containing 1.5 kg of acetaminophen, 2.7 kg of salicylamide, 0.6 kg of anhydrous caffeine, and a disintegrating agent and an excipient supplied into a stirring granulator, and the mixture was stirred and blended. The resulting kneaded product was extruded through a hole having a diameter of φ0.7 mm, and a granule was obtained by an extrusion granulation method. The granule was dried according to a conventional method, and a particle size of the granule was adjusted with a power mill having a knife and a basket which rotate at a high speed, thereby to obtain a granule having better appearance.

When a disintegration test was performed using water as a test solution, the resulting granule preparation of φ0.7 mm, showed rapid dissolving property of 30 seconds or shorter, and there was obtained a granule having such a strength that abrasion and pulverization do not occur in the coating procedure under vigorous flowing with a fluidized bed coating apparatus shown in the coating of fine particles of Example 2. In this granule, no change in appearance and solubility was recognized after 6 months.

2. Tablet

The PVA copolymer having a polymerization degree of 500 obtained in Production Example was formulated into a 5 weight % aqueous solution, and 0.9 kg of the 5 weight % aqueous solution was added to a mixed powder containing 0.3 kg of acetaminophen, 1.89 kg of lactose and 0.81 kg of corn starch supplied into a stirring granulator, and then the mixture was blended with stirring. The resulting granule was dried in a fluidized bed, and its particle size was adjusted with a power mill. 0.5 weight % magnesium stearate was added to the granule, followed by mixing. Using the granule for tableting, an uncoated tablet having φ7 mm, a weight of 125 mg and a thickness of 2.85 mm was obtained with a rotary tableting machine.

A hardness of the resulting uncoated tablet was 50 N, appearance defect such as a crack and a breakage of a tablet was not recognized, and a disintegration time using water as a test solution was 2 minutes, demonstrating it to be a rapid disintegration property. No change in appearance and solubility of this tablet was recognized after 6 months.

Industrial Applicability

The resin composition of the present invention can be utilized as a coating agent for medicines, drugs for animals, agricultural chemicals, fertilizers or foods.

The invention claimed is:

1. An aqueous coating solution, comprising a copolymer consisting of a partially hydrolyzed polyvinyl alcohol having an average polymerization degree of 300 to 500 and a polymerizable vinyl monomer in a weight ratio of 6:4 to 9:1,
wherein:
the polymerizable vinyl monomer consists of acrylic acid and methyl methacrylate combined in a weight ratio of 3:7 to 0.5:9.5 in the copolymer,
the weight ratio of the partially hydrolyzed polyvinyl alcohol having an average polymerization degree of 300 to 500, the methyl methacrylate and the acrylic acid is 60 to 90: 7 to 38: 0.5 to 12, and
the partially hydrolyzed polyvinyl alcohol excludes a thiol modified polyvinyl alcohol
the aqueous coating solution excludes any other polyvinyl alcohol.

2. The aqueous coating solution according to claim 1, wherein the partially hydrolyzed polyvinyl alcohol has a hydrolyzation degree of 60 to 96 mole %.

3. An aqueous coating solution, comprising a copolymer consisting of a partially hydrolyzed polyvinyl alcohol having an average polymerization degree of 300 to 500 and a polymerizable vinyl monomer in a weight ratio of 6:4 to 9:1,
wherein:
the polymerizable vinyl monomer consists of acrylic acid and methyl methacrylate combined in a weight ratio of 3:7 to 0.5:9.5 in the copolymer, and
the partially hydrolyzed polyvinyl alcohol excludes a thiol modified polyvinyl alcohol
the aqueous coating solution excludes any other polyvinyl alcohol.

4. The aqueous coating solution according to claim 3, wherein the partially hydrolyzed polyvinyl alcohol has a hydrolyzation degree of 60 to 96 mole %.

5. An aqueous binder solution, comprising a copolymer consisting of a partially hydrolyzed polyvinyl alcohol having an average polymerization degree of 300 to 500 and a polymerizable vinyl monomer in a weight ratio 6:4 to 9:1,
wherein:
the polymerizable vinyl monomer consists of acrylic acid and methyl methacrylate combined in a weight ratio 3:7 to 0.5:9.5 in the copolymer, and
the partially hydrolyzed polyvinyl alcohol excludes a thiol modified polyvinyl alcohol
the aqueous binder solution excludes any other polyvinyl alcohol.

6. An aqueous coating suspension, comprising a copolymer consisting of a partially hydrolyzed polyvinyl alcohol having an average polymerization degree of 300 to 500 and a polymerizable vinyl monomer in a weight ratio of 6:4 to 9:1,
wherein:
the polymerizable vinyl monomer consists of acrylic acid and methyl methacrylate combined in a weight ratio of 3:7 to 0.5:9.5 in the copolymer,
the weight ratio of the partially hydrolyzed polyvinyl alcohol having an average polymerization degree of 300 to 500, the methyl methacrylate and the acrylic acid is 60 to 90:7 to 38:0.5 to 12, and
the partially hydrolyzed polyvinyl alcohol excludes a thiol modified polyvinyl alcohol
the aqueous coating suspension excludes any other polyvinyl alcohol.

7. The aqueous coating suspension according to claim 6, wherein the partially hydrolyzed polyvinyl alcohol has a hydrolyzation degree of 60 to 96 mole %.

8. An aqueous coating suspension, comprising a copolymer consisting of a partially hydrolyzed polyvinyl alcohol having an average polymerization degree of 300 to 500 and a polymerizable vinyl monomer in a weight ratio of 6:4 to 9:1,
wherein:
the polymerizable vinyl monomer consists of acrylic acid and methyl methacrylate combined in a weight ratio of 3:7 to 0.5:9.5 in the copolymer, and
the partially hydrolyzed polyvinyl alcohol excludes a thiol modified polyvinyl alcohol
the aqueous coating suspension excludes any other polyvinyl alcohol.

9. The aqueous coating suspension according to claim 8, wherein the partially hydrolyzed polyvinyl alcohol has a hydrolyzation degree of 60 to 96 mole %.

10. An aqueous binder suspension comprising a copolymer consisting of a partially hydrolyzed polyvinyl alcohol having an average polymerization degree of 300 to 500 and a polymerizable vinyl monomer in a weight ratio 6:4 to 9:1,
wherein:
the polymerizable vinyl monomer consists of acrylic acid and methyl methacrylate combined in a weight ratio 3:7 to 0.5:9.5 in the copolymer, and the partially hydrolyzed polyvinyl alcohol excludes a thiol modified polyvinyl alcohol the aqueous binder suspension excludes any other polyvinyl alcohol.

11. An organic solvent coating solution, comprising a copolymer consisting of a partially hydrolyzed polyvinyl alcohol having an average polymerization degree of 300 to 500 and a polymerizable vinyl monomer in a weight ratio of 6:4 to 9:1, wherein:

the polymerizable vinyl monomer consists of acrylic acid and methyl methacrylate combined in a weight ratio of 3:7 to 0.5:9.5 in the copolymer, the weight ratio of the partially hydrolyzed polyvinyl alcohol having an average polymerization degree of 300 to 500, the methyl methacrylate and the acrylic acid is 60 to 90:7 to 38:0.5 to 12, and the partially hydrolyzed polyvinyl alcohol excludes a thiol modified polyvinyl alcohol the organic solvent coating solution excludes any other polyvinyl alcohol.

12. The organic solvent coating solution according to claim 11, wherein the partially hydrolyzed polyvinyl alcohol has a hydrolyzation degree of 60 to 96 mole %.

13. An organic solvent coating solution, comprising a copolymer consisting of a partially hydrolyzed polyvinyl alcohol having an average polymerization degree of 300 to 500 and a polymerizable vinyl monomer in a weight ratio of 6:4 to 9:1, wherein:

the polymerizable vinyl monomer consists of acrylic acid and methyl methacrylate combined in a weight ratio of 3:7 to 0.5:9.5 in the copolymer, and the partially hydrolyzed polyvinyl alcohol excludes a thiol modified polyvinyl alcohol the organic solvent coating solution excludes any other polyvinyl alcohol.

14. The organic solvent coating solution according to claim 13, wherein the partially hydrolyzed polyvinyl alcohol has a hydrolyzation degree of 60 to 96 mole %.

15. An organic solvent binder solution comprising a copolymer consisting of a partially hydrolyzed polyvinyl alcohol having an average polymerization degree of 300 to 500 and a polymerizable vinyl monomer in a weight ratio 6:4 to 9:1, wherein:

the polymerizable vinyl monomer consists of acrylic acid and methyl methacrylate combined in a weight ratio 3:7 to 0.5:9.5 in the copolymer, and the partially hydrolyzed polyvinyl alcohol excludes a thiol modified polyvinyl alcohol the organic solvent binder solution excludes any other polyvinyl alcohol.

16. An organic solvent coating dispersion, comprising a copolymer consisting of a partially hydrolyzed polyvinyl alcohol having an average polymerization degree of 300 to 500 and a polymerizable vinyl monomer in a weight ratio of 6:4 to 9:1, wherein:

the polymerizable vinyl monomer consists of acrylic acid and methyl methacrylate combined in a weight ratio of 3:7 to 0.5:9.5 in the copolymer, the weight ratio of the partially hydrolyzed polyvinyl alcohol having an average polymerization degree of 300 to 500, the methyl methacrylate and the acrylic acid is 60 to 90:7 to 38:0.5 to 12, and the partially hydrolyzed polyvinyl alcohol excludes a thiol modified polyvinyl alcohol the organic solvent coating dispersion excludes any other polyvinyl alcohol.

17. The organic solvent coating dispersion according to claim 16, wherein the partially hydrolyzed polyvinyl alcohol has a hydrolyzation degree of 60 to 96 mole %.

18. An organic solvent coating dispersion, comprising a copolymer consisting of a partially hydrolyzed polyvinyl alcohol having an average polymerization degree of 300 to 500 and a polymerizable vinyl monomer in a weight ratio of 6:4 to 9:1, wherein:

the polymerizable vinyl monomer consists of acrylic acid and methyl methacrylate combined in a weight ratio of 3:7 to 0.5:9.5 in the copolymer, and the partially hydrolyzed polyvinyl alcohol excludes a thiol modified polyvinyl alcohol the organic solvent coating dispersion excludes any other polyvinyl alcohol.

19. The organic solvent coating dispersion according to claim 18, wherein the partially hydrolyzed polyvinyl alcohol has a hydrolyzation degree of 60 to 96 mole %.

20. An organic solvent binder dispersion comprising a copolymer consisting of a partially hydrolyzed polyvinyl alcohol having an average polymerization degree of 300 to 500 and a polymerizable vinyl monomer in a weight ratio 6:4 6 to 9:1, wherein:

the polymerizable vinyl monomer consists of acrylic acid and methyl methacrylate combined in a weight ratio 3:7 to 0.5:9.5 in the copolymer, and the partially hydrolyzed polyvinyl alcohol excludes a thiol modified polyvinyl alcohol the organic solvent binder dispersion excludes any other polyvinyl alcohol.

* * * * *